United States Patent
Kim

(10) Patent No.: US 10,377,931 B2
(45) Date of Patent: Aug. 13, 2019

(54) BIO-INSPIRED POLYMER AND GLUE INCLUDING THE POLYMER

(71) Applicant: RESEARCH & BUSINESS FOUNDATION SUNGKYUNKWAN UNIVERSITY, Suwon-si, Gyeonggi-do (KR)

(72) Inventor: Ji Heung Kim, Suwon-si (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 0 days.

(21) Appl. No.: 15/841,571

(22) Filed: Dec. 14, 2017

(65) Prior Publication Data
US 2018/0163105 A1    Jun. 14, 2018

(30) Foreign Application Priority Data
Dec. 14, 2016  (KR) .................. 10-2016-0170094

(51) Int. Cl.
| | | |
|---|---|---|
| *A61L 24/00* | (2006.01) | |
| *A61L 24/04* | (2006.01) | |
| *C08G 69/08* | (2006.01) | |
| *C08G 69/48* | (2006.01) | |
| *C08G 73/10* | (2006.01) | |
| *C08L 77/04* | (2006.01) | |
| *C09J 177/02* | (2006.01) | |

(52) U.S. Cl.
CPC ......... *C09J 177/02* (2013.01); *A61L 24/0042* (2013.01); *A61L 24/046* (2013.01); *C08G 69/08* (2013.01); *C08G 69/48* (2013.01); *C08G 73/1092* (2013.01)

(58) Field of Classification Search
CPC ......... C09J 177/02; A61L 24/00; A61L 24/06; C08G 69/08; C08G 69/14; C08L 77/02
See application file for complete search history.

(56) References Cited

PUBLICATIONS

An et al. (Polym Int 2011; 60: 1581-1586).*
Mussel-mimetic self-healing polyaspartamide derivative gel via boron-catechol interactions, B. Wang et al., eXPRESS Polymer Letters vol. 9, No. 9 (2015) p. 799-808.

* cited by examiner

*Primary Examiner* — Shane Fang
(74) *Attorney, Agent, or Firm* — NSIP Law

(57) ABSTRACT

The present invention provides a bio-inspired polymer compound, and a bio-adhesive having the same, and more particularly, to a bio-inspired polymer compound having biocompatibility and high adhesion ability, and a bio-adhesive comprising the same, wherein as the bio-inspired polymer compound absorbs water, the bio-inspired polymer compound becomes viscous in a swollen state, wherein the bio-inspired polymer compound has repeating units, a unit expressed by Chemical Formula 1 and a unit represented by Chemical Formula 2.

8 Claims, 6 Drawing Sheets

BIO-INSPIRED POLYMER AND GLUE INCLUDING THE POLYMER

CROSS-REFERENCE TO RELATED APPLICATION

This application claims the benefit of Korean Patent Application No. 10-2016-0170094 filed on Dec. 14, 2016, the entire content of which is incorporated herein by reference.

FIELD OF THE INVENTION

The present disclosure relates to a bio-inspired polymer compound, and a bio-adhesive comprising the same, and more particularly, to a bio-inspired polymer compound having biocompatibility and high adhesion ability, and a bio-adhesive comprising the same.

BACKGROUND OF THE INVENTION

Adhesion refers to the resistance force required to separate two contact surfaces. The adhesive force corresponding to the resistance force is affected by the properties of the facing surfaces, the chemicals thereof, the micro-environment of the interface, and the like. In particular, wet adhesion refers to adhesion occurring in a wet environment. Synthetic adhesives, which are widely used for the wet adhesion, have the disadvantage that adhesion is weakened by moisture or other contaminants, and adhesion thereof to various surfaces is deteriorated.

As an approach to overcoming this problem, there is a growing interest in bio-inspired adhesives with excellent strength, moisture impermeability and rigidity. Among the bio-inspired adhesives, the area of greatest interest is the use of adhesive proteins secreted by the sea mussels. The mussels secrete adhesive proteins on the surface of natural or artifact structures in the sea, making them strongly adherent thereto in harsh environments. The strong adhesion of these mussels is known to be attributed to the catechol-containing amino acids which is 3,4-dihydroxyphenylalanine referred to as DOPA as found in the adhesive protein structure secreted by the mussel leg tissue.

Currently, the DOPA is known to be an essential component of byssal proteins, which act as cohesive and adhesive. In this technical area, there is a continuing effort to design peptide compounds or polymers with relatively simple structures containing catheter functional groups included in DOAP or DOPA.

As the early examples of the mussel-inspired polymer, DOPA polypeptides were chemically synthesized using solid or liquid peptide substances. Later, polypeptide copolymers of DOPA and lysine were synthesized by ring opening polymerization of NCA monomers. DNA recombination techniques have also been introduced to produce adhesive proteins. Commonly used synthetic methods includes the modification of DOPA, DOPA peptides, or other catechol functional groups to linear or branched polymers using well-known chemical bonding reactions. This approach may be found, for example, in the linear or branched polymers based on polyethylene glycol (PEG) having the DOAP incorporated into the end of the chain thereof. Alternatively, there is a direct synthesis of the bio-adhesive polymer via the polymerization of DOPA or catechol-containing monomers.

Meanwhile, many bio-adhesives have been known to date. However, since such bio-adhesives generally do not exhibit excellent adhesion properties to all materials, appropriate bio-adhesives should be selected depending on the material of the adhesive substrate or the substrate to be adhered or the purpose of the adhesion.

SUMMARY OF THE INVENTION

One aspect of the present invention provides a biocompatible bio-inspired polymer compound that exhibits high adhesion to a variety of substrates and has biocompatibility.

Another aspect of the present disclosure provides a bio-adhesive comprising the bio-inspired polymer compound.

In a first aspect of the present disclosure, there is provided a bio-inspired polymer compound comprising, as repeating units, a unit expressed by a following Chemical Formula 1 and a unit represented by a following Chemical Formula 2:

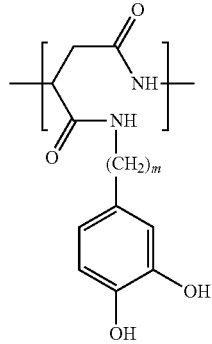

<Chemical Formula 1>

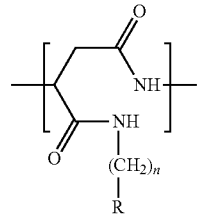

<Chemical Formula 2> wherein, in the Chemical Formula 1, m represents a natural number of 1 to 6;

in the Chemical Formula 2, n represents a natural number of 1 to 11; and in the Chemical Formula 2, R represents a methyl group (—$CH_3$), a carboxyl group (—COOH) or a hydroxyl group (—OH).

In one embodiment of the bio-inspired polymer compound, in the Chemical Formula 2, n represents 7, and R represents a methyl group (—$CH_3$).

In one embodiment of the bio-inspired polymer compound, a weight average molecular weight of the bio-inspired polymer compound in a range from $10^4$ g/mol to $10^5$ g/mol.

In one embodiment of the bio-inspired polymer compound, a molar ratio between the unit represented by the Chemical Formula 1 and the unit represented by the Chemical Formula 2 is in a range of 1:4 to 4:1.

In a second aspect of the present disclosure, there is provided a bio-adhesive comprising a bio-inspired polymer compound, wherein the compound comprises, as repeating units, a unit expressed by a following Chemical Formula 1 and a unit represented by a following Chemical Formula 2:

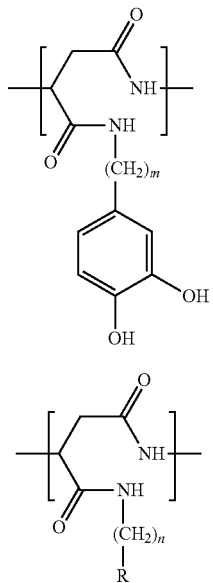

<Chemical Formula 1>

<Chemical Formula 2> wherein, in the Chemical Formula 1, m represents a natural number of 1 to 6;

in the Chemical Formula 2, n represents a natural number of 1 to 11; and in the Chemical Formula 2, R represents a methyl group (—CH$_3$), a carboxyl group (—COOH) or a hydroxyl group (—OH), provided, when the bio-inspired polymer compound absorbs water, the bio-inspired polymer compound is brought into being viscous in a swollen state.

In one embodiment of the bio-adhesive, in the Chemical Formula 2, n represents 7, and R represents a methyl group (—CH$_3$).

In one embodiment of the bio-adhesive, a weight average molecular weight of the bio-inspired polymer compound in a range from $10^4$ g/mol to $10^5$ g/mol.

In one embodiment of the bio-adhesive, a molar ratio between the unit represented by the Chemical Formula 1 and the unit represented by the Chemical Formula 2 is in a range of 1:4 to 4:1.

In one embodiment of the bio-adhesive, the bio-adhesive has an adhesive strength of at least 0.3 MPa to a metal foil or glass substrate.

In one embodiment of the bio-adhesive, the bio-adhesive has an adhesive strength of at least 0.15 MPa to a plastic substrate.

The bio-inspired polymer compounds of the present disclosure and the bio-adhesives containing the same have high adhesion to a wide variety of substrates such as paper, ceramics, glass, metals, and at the same time are non-toxic, non-antigenic and biodegradable. The bio-inspired polymer compounds according to the present disclosure may be widely used for bio-adhesives in a variety of technical fields and are particularly well suited for application to tissue bio-adhesives and sealants in medical applications.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTION OF THE INVENTION

Figure 1:
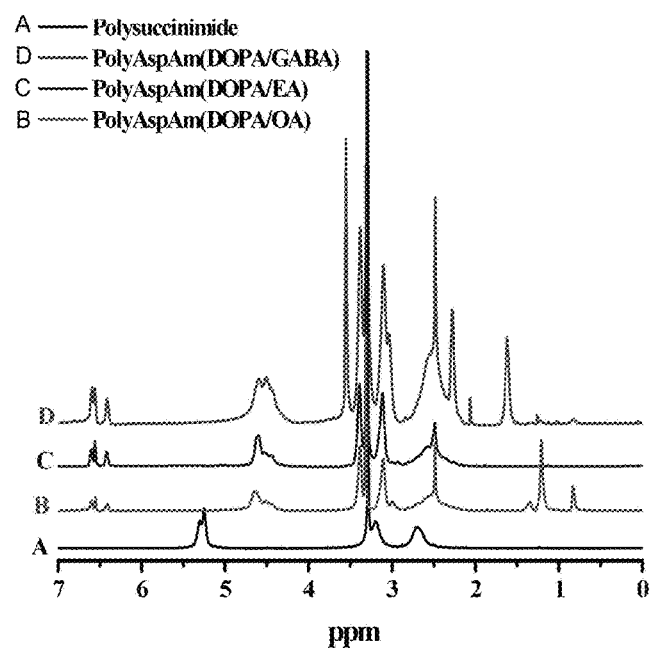
FIG. 1 is a view showing an analysis result of polymer samples according to the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

In the bio-inspired polymer compound and the bio-adhesive comprising the same according to the present disclosure, the bio-inspired polymer compound contains, as repeating units, a unit expressed by the following Chemical Formula 1 and a unit represented by the following Chemical Formula 2:

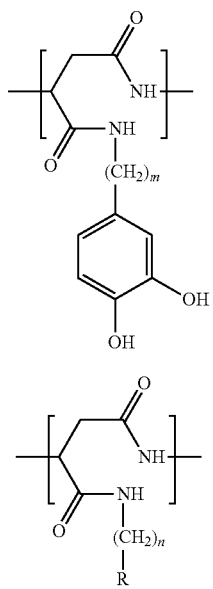
<Chemical Formula 1>

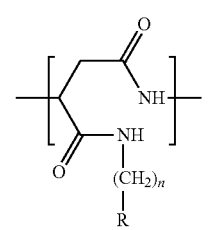
<Chemical Formula 2> wherein, in the Chemical Formula 1, m represents a natural number of 1 to 6;

in the Chemical Formula 2, n represents a natural number of 1 to 11;

in the Chemical Formula 2, R represents a methyl group (—$CH_3$), a carboxyl group (—COOH) or a hydroxyl group (—OH).

The repeating units including the unit represented by the Chemical Formula 1 and the unit represented by the Chemical Formula 2 may include the repeating arrangement of the units represented by the Chemical Formula 1 and subsequent repetitive arrangement of the units represented by the Chemical Formula 2. Alternatively or additionally, the repeating units including the unit represented by the Chemical Formula 1 and the unit represented by the Chemical Formula 2 may include iterations of the alternating arrangements between the unit represented by Chemical Formula 1 and the unit represented by Chemical Formula 2.

The backbone of the bio-inspired polymer compound according to the present disclosure may be based on a polyaspartic acid. By including the polyaspartic acid backbone, the bio-inspired polymer compound according to the present disclosure may be biocompatible.

The terminal group connected to the unit represented by Chemical Formula 1 has a structure similar to that of the mussel-inspired adhesive protein. As a result, the bio-inspired polymer compound according to the present disclosure may be applied for a bio-adhesive having a high biocompatibility and eco-friendliness because the bio-inspired polymer compound according to the present disclosure includes the unit represented by Chemical Formula 1.

In one embodiment, in the Chemical Formula 2 of the bio-inspired polymer compound according to the present disclosure, n represents a natural number of 5 to 7, and R represents a methyl group. In this case, high adhesion strength can be realized. That is, when R is a methyl group, the polymer represents a higher bonding strength as compared with the case where R is the carboxyl group or a hydroxyl group. Particularly, the high bonding strength achieved when R is a methyl group may be realized not only to various substrates such as aluminum foil, glass, paper, but also to various plastic substrates. This is because, when R is a hydrophobic alkyl group which is not a hydrophilic group such as a carboxyl group or a hydroxyl group, intermolecular hydrophobic mutual attraction is increased, and adhesion is greatly improved by reducing the water layer existing between the bio-adhesive and the substrate.

In a bio-inspired polymer compound according to the present disclosure, the molar ratio between the unit represented by Chemical Formula 1 and the unit represented by Chemical Formula 2 may be in a range of 1:4 to 4:1.

The weight average molecular weight of the bio-inspired polymer compound according to the present disclosure may range from $10^4$ g/mol to $10^5$ g/mol.

The bio-inspired polymer compounds according to the present disclosure have hydrophilicity. The bio-inspired polymer compound has a property of swelling by absorbing water. Thus, since the polymer compound has a high viscosity in a swollen state, it may be used as a wet bio-adhesive in the form of a sticky glue.

The bio-inspired polymer compound may be prepared using the aminolysis reaction of polysuccinimide (PSI). That is, by reacting the polysuccinimide (PSI) with a first compound comprising a functional group contained in the unit represented by the Chemical Formula 1 and a second compound including a functional group contained in the unit represented by the Chemical Formula 2, the bio-inspired polymer compound may be prepared.

The first compound includes a compound represented by the following Chemical Formula 3:

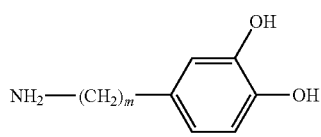
Chemical Formula 3 wherein, m represents a natural number of 1 to 6.

The second compound includes alkylamine ($R_1$—$NH_2$, wherein $R_1$ represents an alkyl group having 1 to 12 carbon atoms), alkanolamine (HO—$(CH_2)_x$—$NH_2$, wherein x represents a natural number of 1 to 12), or aminoalkyl acid (HOOC—$(CH_2)_y$—$NH_2$, wherein y represents a natural number from 1 to 11).

The production method of the polysuccinimide is not particularly limited. In an example, the polysuccinimide may be produced by polymerization reaction such as bulk polymerization or polycondensation of the asphalt acid.

The polysuccinimide may be mixed with the first compound and the second compound and then the resulting mixture may be subjected to ring-opening reaction under solvent conditions, thereby preparing the bio-inspired polymer compound according to the present disclosure. The solvent conditions may employ DMF, DMSO or NMP.

Hereinafter, the present disclosure will be described in more detail via production examples and characterization of samples manufactured by the production examples.

Production Example 1: Preparation of Polysuccinimide (PSI)

30 g of L-aspartic acid and 30 g of 98% ortho-phosphoric acid were input into a round bottom flask at a weight ratio of 50:50 and were mixed at room temperature in the flask to form a first mixture. The first mixture was slowly heated from room temperature to 180 DEG C. for 30 minutes under reduced pressure. Thereafter, it was maintained at 180 DEG C. for 4.5 hours. The reacted first mixture was cooled. Then, DMF was added to the cooled mixture which in turn is dissolved to prepare a first solution. The first solution prepared thus was precipitated using an excess of water. The precipitate was washed several times with water, and, thus, the remaining phosphoric acid was removed until the solution reached a pH of 7. Finally, the resulting product was dried under vacuum at 70 DEG C. for 3 days to yield the PSI in the form of a white powder. The molecular weight of the PSI obtained thus was calculated from an experimental formula related to the solution viscosity and molecular weight. The molecular weight thereof was estimated to be about 75,000 Da.

Production Example 2: Preparation of Polymer Sample 1 (DOPA/GABA)

First, γ-aminobutyric methyl ester hydrochloride (GABAME) was synthesized from γ-aminobutyric acid (GABA) as follows: 0.01 mol of GABA was weighed into a round bottom flask and dissolved in 30 mL of methanol to produce a first solution. Then, 0.02 mol of chlorotrimethylsilane was slowly added to the first solution being slowly stirred using the magnet to produce a second solution. The second solution was stirred at room temperature for 24 hours and was precipitated using ethyl alcohol. The precipitates were filtered to obtain powders which in turn were washed several times with fresh ethyl ether and then were dried under vacuum to obtain the GABAME.

The PSI (0.97 g corresponding to 0.01 mol of succinimide unit) prepared in the production example 1 was dissolved in 20 mL of DMF (N, N-dimethylformamide (99.8% anhydrous)). Thus, a PSI solution was prepared. The GABAME (0.66 g, 6.5 mmol) and dibutylamine (1.1 mL, 6.5 mmol) were dissolved in 20 mL of DMF. As a result, a GABAME solution was prepared. The GABAME solution was vigorously stirred at room temperature. The GABAME solution was added to the PSI solution to prepare a first mixture. After the first mixture was reacted with each other for 5 days, 0.01 mol of DOPA (dopamine hydrochloride) and 0.005 mol of DBA (dibutylamine) were added to the first mixture. Thereby, a second mixture was produced. The mixing reaction in the second mixture was performed in a nitrogen atmosphere in the presence of 0.05 g of sodium hydrosulfite. The reacted second mixture was placed in an 80° C. water bath and stirred for 24 hours. Then, the second mixture was then precipitated in 300 mL of cold acetone. A product as the polymer sample 1 (DOPA/GABA) was separated from the precipitated product by filtration.

The product thus obtained was dispersed in a pH 10 solution of sodium hydroxide in distilled water. Thereby, a dispersion was prepared. An additional sodium hydroxide solution was dropped into the dispersion to maintain the pH at about 10 thereof. The dispersion was stirred overnight, and then hydrochloric acid was added to the dispersion until stabilized to pH 4. The resulting dispersion solution was filtered, dialyzed and freeze-dried to obtain a solid-state polymer sample 1.

Production Example 3: Preparation of Polymer Sample 2 (DOPA/EA)

PSI (0.97 g corresponding to 0.01 mol of succinimide unit) prepared via the production example 1 was dissolved in 20 mL of DMF. Thereby, a PSI solution is prepared. 1.6 g of DOPA and 3.6 mL of DBA were added to the PSI solution. Thereby, a first mixture is produced. The reaction in the first mixture was carried out in a nitrogen atmosphere in the presence of sodium hydrosulfite (0.05 g). Then, the reacted first mixture was placed in an 80° C. water bath and stirred for 24 hours. Then, 0.3 mL of EA (ethanolamine) was slowly added to the first mixture. Thereby, a second mixture was produced. The second mixture was further stirred at room temperature for 24 hours. Then, the second mixture was precipitated in 300 mL of cold acetone. The resulting precipitate was filtered and the thus-resulting product was dried in an oven at 40° C. for 3 days. Thus, the polymer sample 2 was prepared.

Production Example 4: Preparation of Polymer Sample 3 (DOPA/OA)

Polymer sample 3 was prepared by substantially the same method as in the production example 3 except that 0.65 g of OA (octyl amine) was used instead of EA.

Production Example 5: Preparation of Polymer Sample 4 (DOPA/HA)

Polymer Sample 4 was prepared by substantially the same method as in the production example 3, except that 0.51 g of HA (hexyl amine) was used instead of EA.

Structure Analysis $^1$H NMR analysis was performed on the polysuccinimide and polymer samples 1 to 3 prepared respectively through the production examples 1 to 4 above. The results thereof are shown in FIG. 1.

FIG. 1 is a view showing an analysis result of the polymer samples.

In FIG. 1, (a) indicates an analysis graph, and (b) indicates a table showing contents of DOPA and amine compound in each sample as calculated from the $^1$H NMR analysis result. In (a), A represents polysuccinimide, B represents the polymer sample 3 (DOPA/OA), C represents the polymer sample 2 (DOPA/EA), and D represents the polymer sample 1 (DOPA/GABA).

Referring to FIG. 1 (a), it may be seen that the methine proton (5.3 ppm) of the initial succinimide ring disappeared completely via the amination reaction, as shown in the graphs of A to D. From this, it may be deduced that the succinimide ring is opened such that polyastatic-based derivatives are produced.

Referring to FIG. 1 (a), as shown in the graphs of B to D, the aromatic protons of the dopamine phenyl group appear as three peaks at about 6.5 ppm. The two peaks at 1.6 ppm and 2.2 ppm are due to the methylene protons of GABA, while the three peaks at 0.8 ppm, 1.1 ppm and 1.2 ppm are due to the methylene protons of the methylamine.

Referring to FIG. 1 (b), the following facts are observed through the 1H NMR analysis: the polymer sample 1 has a structure in which DOPA and GABA are linked to each other at mol % of 49:51; the polymer sample 2 has a structure in which DOPA and EA are linked to each other at mol % of 47:53; and the polymer sample 3 has a structure in which DOPA and OA are linked to each other at mol % of 52:48.

Evaluation of Water Absorption Ability

Each of the polymer samples 1 to 3 prepared above was swelled in distilled water to prepare swelled bio-adhesives. First, the weight ($W_d$) of the dried polymer powder was measured. The dried polymer samples were placed in distilled water until they reach close to equilibrium swelling.

The weight ($W_d$) of the dried polymer powder is subtracted from the weight of the swollen gel ($W_s$). Thus, the pure weight of the water as absorbed by the polymer was obtained as $W_s-W_d$. The water absorption capacity was calculated according to the following equation (1):

$$\text{water absorption} = \frac{(W_s - W_d)}{W_d} \quad \text{[Equation 1]}$$

Figure 2:
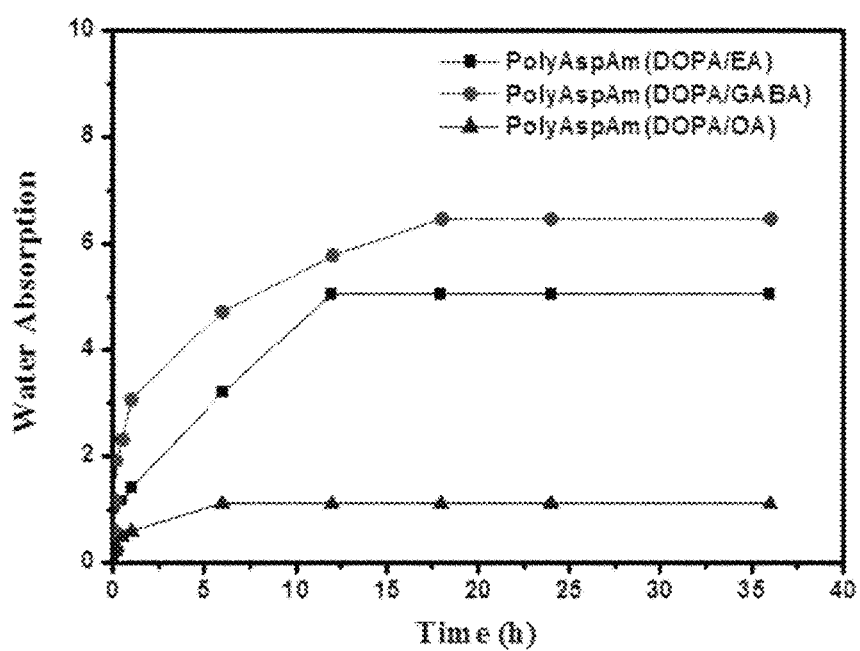
FIG. 2 is a graph showing the results of evaluating the water absorption capability of polymer samples according to the present disclosure.

The results are shown in FIG. 2.

FIG. 2 is a graph showing the results of evaluation of the water absorption capability of the polymer samples.

Referring to FIG. 2, it may be seen that all of the lyophilized bio-adhesive samples containing the polymer samples 1 to 3 exhibit typical moisture absorption performance curves.

It may be seen that, in the polymer sample 3 including the octyl group having the hydrophobic property, the water absorption ability is relatively lower than that of the other polymer samples. In this polymer sample 3, it may be seen that swelling appears to reach equilibrium after about 5 hours.

On the other hand, the water absorption capacity of the polymer samples 1 and 2 is 4 to 5 times higher than that of the polymer sample 3 because the polymer samples 1 and 2 has the hydrophilic property by the hydroxy or carboxyl group contained therein as their functional groups. In the polymer samples 1 and 2, it is confirmed that swelling equilibrium is reached after about 12 hours to about 7 hours.

Adhesiveness Evaluation 0.05 g of the polymer sample 3 and 0.05 mL of distilled water were mixed to prepare a bio-adhesive. In order to confirm the adhesive property of the adhesive, the adhesive was placed between the fingers, the fingers were bonded to each other, and then the picture was taken after the separation. This process is imaged using an imaging device. The result is shown in FIG. 3.

Figure 3:
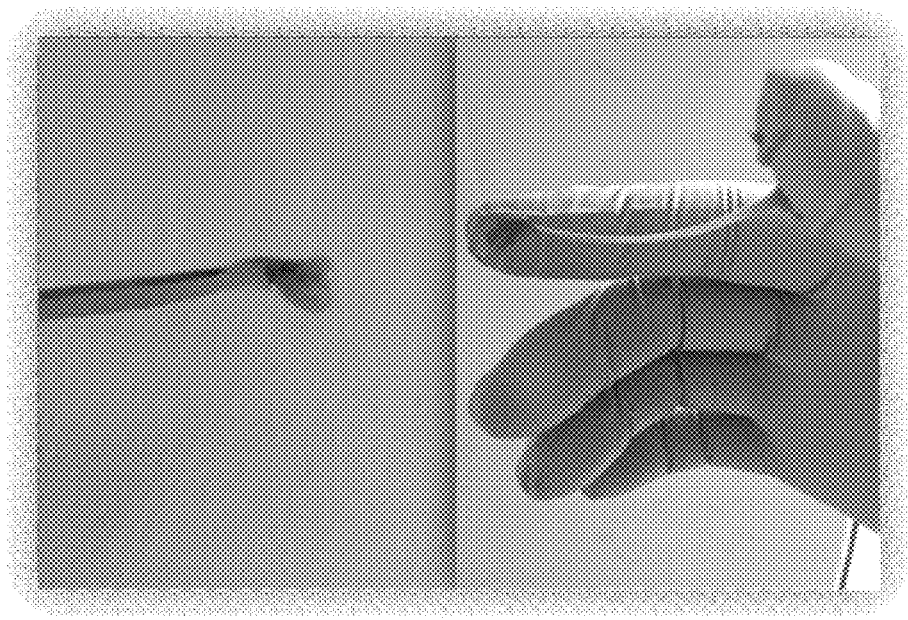
FIG. 3 is a view showing an actual image of a bio-adhesive according to the present disclosure.

FIG. 3 is a view showing an actual image of the bio-adhesive according to the present disclosure.

Referring to FIG. 3, it may be seen that the produced bio-adhesive has a sticky state and exhibits a yellow color.

Adhesive Strength Evaluation-1

For the evaluation of the adhesive strength of the bio-adhesive using the prepared polymer samples, a lap shear test was performed on a UTM (QC-508E, Cometech, Taiwan) at a rate of 15 mm/min using a 100 N load cell. The adhesive strength is expressed in Pascal (Pa) unit and is obtained by dividing shear force (in Newtons) by the adhered overlapped area. The length of the substrate was 7.5 cm and the adhered area was 2.0 cm×2.5 cm. As the substrate, aluminum foil, glass slide and paper were used. Each polymer sample was mixed with distilled water to make each bio-adhesive. The results are shown in FIG. 4.

Figure 4:
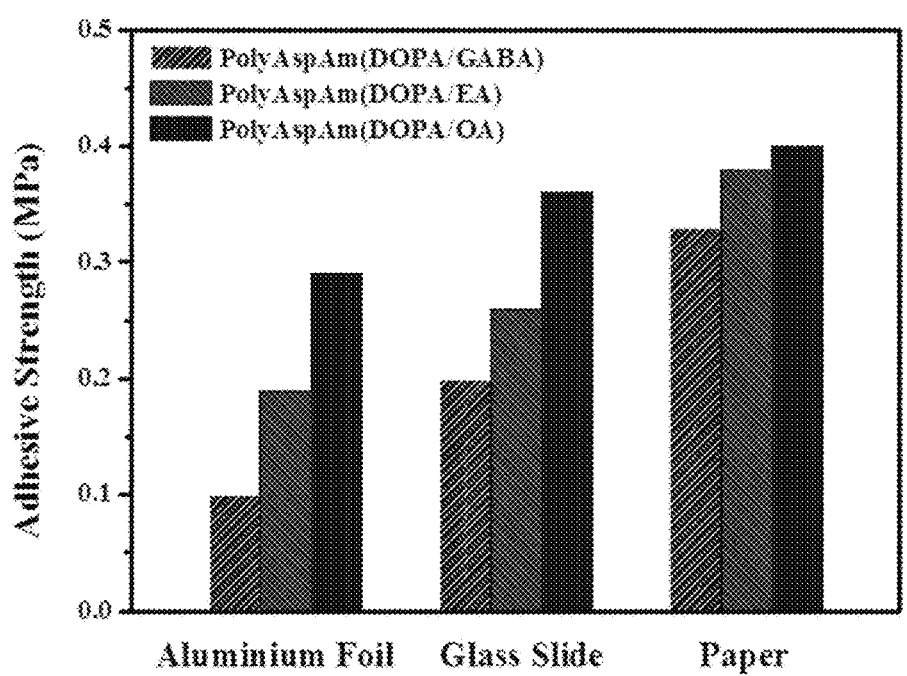
FIG. 4 is a graph showing the adhesive strength of the polymer samples based on the kinds of substrates according to the present disclosure.

FIG. 4 shows the adhesive strength results based on the types of the substrates of the polymer samples.

Referring to FIG. 4, it may be seen that all of the bio-adhesives using the polymer samples 1 to 3 exhibit a high adhesive strength of at least 0.1 MPa or more. It may be seen that the adhesive strength of the adhesive including the polymer samples 1 to 3 to the paper is high.

When the bio-adhesive was fabricated using the polymer sample 3 using OA, it was confirmed that the highest adhesive strength to the three substrates is obtained among the polymer samples 1 to 3. The adhesive using the polymer sample 2 had higher adhesive strength than the adhesive using the polymer sample 1.

Further, the same experiment was performed on polymer sample 4 using EA. The adhesive using the polymer sample 4 using EA showed a little lower adhesive strength than the bio-adhesive prepared using the polymer sample 3. Nevertheless, it was confirmed that the polymer sample 4 using EA showed a high adhesive strength of about 60%. Among the bio-adhesive using the polymer samples 1 to 4, the adhesive strength of the bio-adhesive using the polymer sample 3 is the highest.

In particular, it was found that the adhesive strength of the bio-adhesive using the polymer sample 3 to the metal was about 1.5 to 3 times higher than the adhesive strength of the adhesive using the polymer sample 1 or 2 to the metal. In addition, the adhesive strength of the bio-adhesive using polymer sample 3 to the glass was about twice as high as the adhesive strength of the adhesive using polymer sample 1 or 2 to the glass.

Adhesive Strength Evaluation-2

The adhesive strength of the adhesives using the samples 1 to 3 was evaluated for each of the three different types of plastics, that is, PET, PMMA and PS substrates, in substantially the same manner as in the Adhesive Strength Evaluation-1. The results are shown in FIG. 5.

Figure 5:
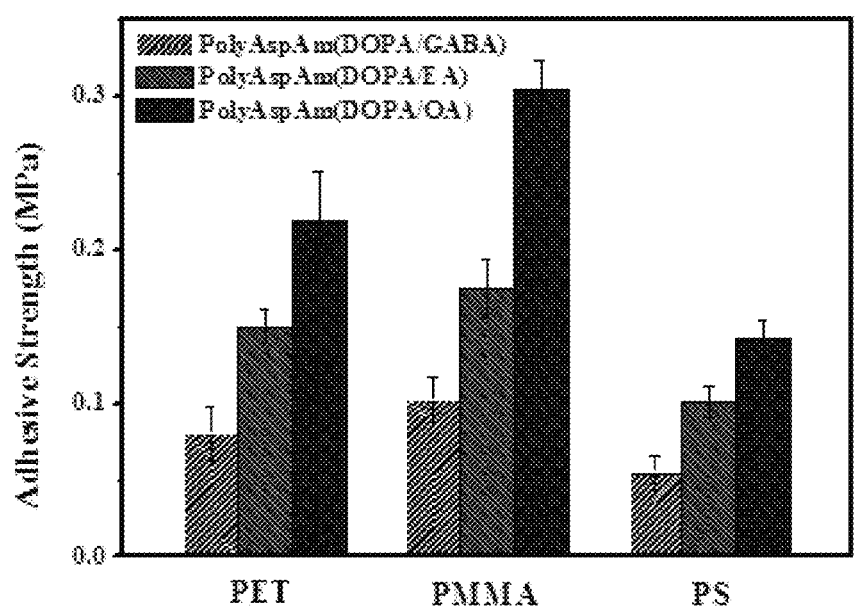
FIG. 5 is a graph showing the adhesive strength of the polymer samples based on the types of plastics of the substrates according to the present disclosure.

FIG. 5 shows the adhesive strength based on plastic types of adhesives using polymer samples.

Referring to FIG. 5, all of the adhesives using the polymer samples 1 to 3 exhibit a certain degree of adhesive strength to the plastic substrate. It may be seen that the adhesive using the polymer sample 3 exhibits an adhesive strength of at least 0.15 MPa or more to all of the PET, PMMA and PS substrates. On the other hand, the adhesive using the polymer sample 2 showed only one half of the adhesive strength of the adhesive using the polymer sample 3. It may be seen that the adhesive using the polymer sample 1 exhibits a relatively low level of the adhesive strength to the PS substrate. The adhesive using the polymer sample 4 exhibits a lower adhesive strength to the plastic than the adhesive using the polymer sample 3. Nevertheless, it may be seen that the adhesive using the polymer sample 4 has higher adhesive strength to the plastic substrate than the bio-adhesive using the polymer sample 1 or 2.

Generally, bio-adhesives with high adhesive strength to plastics are very rare. However, when the bio-adhesive is prepared using the polymer sample 3, it may be confirmed that the higher adhesive strength is achieved regardless of the kinds of the plastics.

Evaluation of Adhesive Strength-3

To measure the adhesive strength to the live skin, the pig skin was cut to be length×width=7.5 cm×2.0 cm. The cut skin pieces were washed with aqueous sodium chloride solution and soaked in PBS buffer solution (pH=7.4) for 12 hours. The adhesives using the samples 1 to 3 were applied on the two pig skin samples thus prepared so that the overlapped area was 2.0 cm×1.5 cm, and then the adhesive strength was measured. The specific adhesive strength evaluation test was performed in substantially the same manner as the adhesive strength evaluation-1. The results are shown in FIG. 6.

Figure 6:
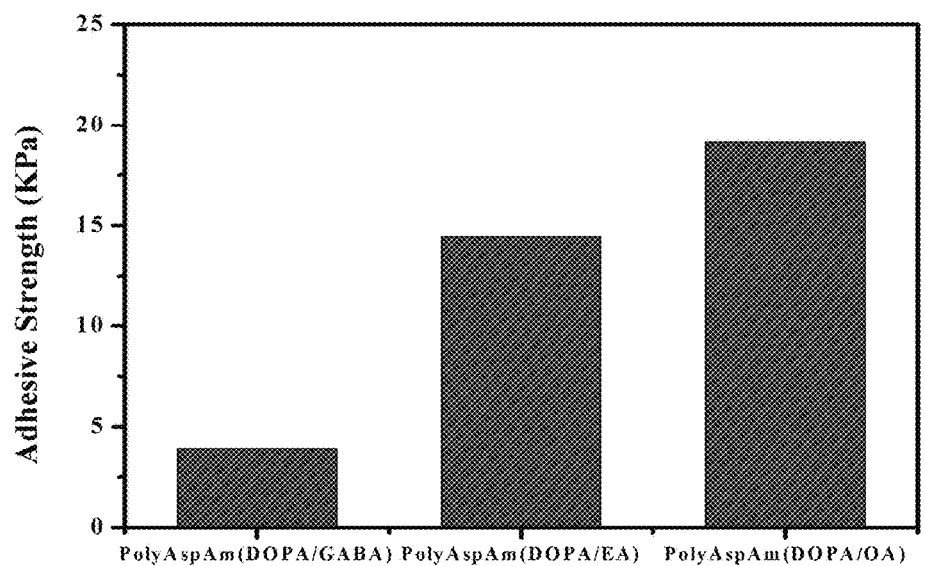
FIG. 6 is a graph showing the adhesion strength of the polymer samples to a pig skin according to the present disclosure.

FIG. 6 is a graph showing the adhesive strength of the adhesives using the polymer samples to the pig skin.

Referring to FIG. 6, the bar graphs in order from left side to right side show the results of evaluation of the adhesive strength of the bio-adhesives using the polymer samples 1, 2 and 3, respectively to the pig skin. It may be seen that the adhesive using the polymer sample 3 has four times higher adhesive strength than the adhesive using the polymer sample 1. It may be seen that the adhesive using the polymer sample 3 has 1.3 times higher adhesive strength than the adhesive using the polymer sample 2. As a result, it may be confirmed that the bio-adhesive using the polymer sample 3 has bio-adhesion property.

Referring to the above experiments and evaluation results, when the adhesive includes the polymer sample 3 in which the functional group connected to the polyaspartic acid-based main chain includes carbon chains having 2 to 12 carbon atoms, it may be confirmed that the adhesive including the sample 3 has a high adhesive strength not only to the metal substrate but also to various plastic substrates and skins. There are many types of bio-adhesives that are specialized to metal substrates. However, there are few bio-adhesives that are specialized to the plastics and skins. In this connection, the bio-adhesive containing polymer sample 3 may be applied to various types of plastics and skin as well as metal substrates. Thus, the bio-adhesive containing the polymer sample 3 may be used as a very useful bio-adhesive.

The above description has been made with reference to the preferred embodiments of the present disclosure. It will be apparent, however, to one skilled in the art that various changes and modifications may be made to the present disclosure without departing from the spirit and scope of the present disclosure as set forth in the following claims.

The invention claimed is:

1. A bio-inspired polymer compound comprising, as repeating units, a unit expressed by a following Chemical Formula 1 and a unit represented by a following Chemical Formula 2:

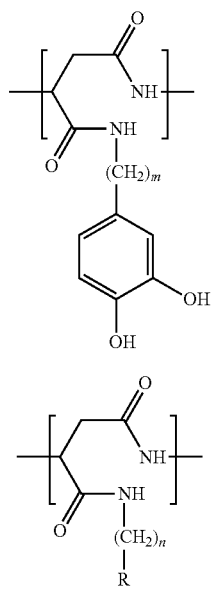

<Chemical Formula 1>

<Chemical Formula 2> wherein,
in the Chemical Formula 1, m represents a natural number of 1 to 6;
in the Chemical Formula 2, n represents a natural number of 1 to 11; and
in the Chemical Formula 2, R represents a methyl group (—$CH_3$), a carboxyl group (—COOH) or a hydroxyl group (—OH), and
wherein a weight average molecular weight of the bio-inspired polymer compound is in a range from $10^4$ g/mol to $10^5$ g/mol.

2. The bio-inspired polymer compound of claim 1, wherein in the Chemical Formula 2, n represents 7, and R represents a methyl group (—$CH_3$).

3. The bio-inspired polymer compound of claim 1, wherein a molar ratio between the unit represented by the Chemical Formula 1 and the unit represented by the Chemical Formula 2 is in a range of 1:4 to 4:1.

4. A bio-adhesive comprising a bio-inspired polymer compound, wherein the compound comprises, as repeating units, a unit expressed by a following Chemical Formula 1 and a unit represented by a following Chemical Formula 2:

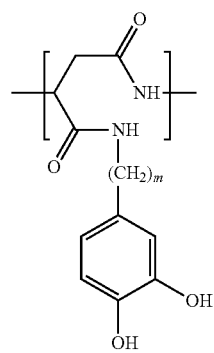

<Chemical Formula 1>

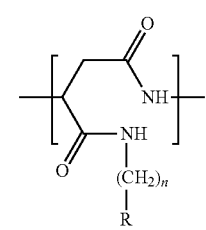

<Chemical Formula 2> wherein,
in the Chemical Formula 1, m represents a natural number of 1 to 6;
in the Chemical Formula 2, n represents a natural number of 1 to 11; and
in the Chemical Formula 2, R represents a methyl group (—$CH_3$), a carboxyl group (—COOH) or a hydroxyl group (—OH),
provided, when the bio-inspired polymer compound absorbs water, the bio-inspired polymer compound becomes viscous in a swollen state, and
wherein a weight average molecular weight of the bio-inspired polymer compound is in a range from $10^4$ g/mol to $10^5$ g/mol.

5. The bio-adhesive of claim 4, wherein in the Chemical Formula 2, n represents 7, and R represents a methyl group (—$CH_3$).

6. The bio-adhesive of claim 4, wherein a molar ratio between the unit represented by the Chemical Formula 1 and the unit represented by the Chemical Formula 2 is in a range of 1:4 to 4:1.

7. The bio-adhesive of claim 5, wherein the bio-adhesive has an adhesive strength of at least 0.3 MPa to a metal foil or glass substrate.

8. The bio-adhesive of claim 5, wherein the bio-adhesive has an adhesive strength of at least 0.15 MPa to a plastic substrate.

\* \* \* \* \*